United States Patent [19]

Warriner

[11] Patent Number: Plant 6,514

[45] Date of Patent: Jan. 3, 1989

[54] ROSE PLANT JACWHIM

[75] Inventor: William A. Warriner, Tustin, Calif.

[73] Assignee: Jackson & Perkins Company, Medford, Oreg.

[21] Appl. No.: 27,685

[22] Filed: Mar. 19, 1987

[51] Int. Cl.[4] ..... A01H 5/00

[52] U.S. Cl. ..... Plt./8

[58] Field of Search ..... Plt./8

*Primary Examiner*—James R. Feyrer

*Attorney, Agent, or Firm*—Majestic, Gallagher, Parsons & Siebert

[57] ABSTRACT

A rose variety of the miniature class is provided having numerous flower clusters of attractive high-centered white flowers, compact dwarf growth habit, rapid rooting and plant growth in pot culture, and resistance to powdery mildew.

1 Drawing Sheet

SUMMARY OF THE INVENTION

The present invention relates to a new and distinct variety of rose plant of the miniature class, which was originated by me by crossing the variety Petticoat, U.S. Plant Pat. No. 5,039, with the variety Red Minimo, U.S. Plant Pat. No. 5,770.

The primary objective of this breeding was to produce a new rose variety of the miniature class that was adaptable to pot culture. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Rapid rooting from cuttings;
2. Rapid growth in pot culture;
3. Compact habit;
4. High centered bud borne in clusters;
5. Clean white flower color;
6. Powdery mildew resistance; and
7. Small glossy dark green leaves.

Asexual reproduction of this new variety by cuttings, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacwhim". Color terminology is in accordance with The Royal Horticultural Society Colour Chart except where an ordinary dictionary significance for the color is apparent.

Observations of the buds and flowers were made from specimens grown in a greenhouse at Irvine, Calif. in January and February.

Flower

The blooming habit is continuous. The bud size is ¾ inches when the petals start to unfurl. The bud form is pointed ovoid. The bud color when sepals first divide is near White 155D; when half blown, the upper side of petals is near White 155D and the lower side of petals is near White 155D. The sepals have a color near Green 138B. The surface texture is covered with fine hairs. There are three appendaged sepals lightly appendaged, and two unappendaged sepals with hairy edge. The receptacle color is near Green 138B with a funnel shape, small size and smooth surface. The peduncle is of short length, and smooth surface. Peduncle color is medium green and the penduncle is stiff, erect and slender.

Bloom

Bloom size is small, with an average open size of two inches, borne in clusters. The clusters are rounded to flat. The stems are strong and short. The form when first open is high center. This form then flattens and the outer petals curl back, quill fashion. Under normal conditions there are 70–90 petals. The upper side of petals is near White 155D, as is the reverse side of the petals. The base of petals has a very small greenish half moon with the major color being near White 155D. There are no variegations. The general tonality at the end of the first day shows no change in color. At the end of the third day, there remains no discoloration.

The fragrance is slight. The petal texture is thin, of a deltoid shape with the tips being slightly recurved.

The arrangement is imbricated with few petaloids in the center. The blooms drop off cleanly, and last on the plant for a fair period and as a cut flower for a fair time.

Reproductive Parts

The anthers are small and few, of yellow color, arranged regularly around the styles and mixed with the petaloids. The filaments are white, the pollen is gold yellow, the styles are green, and the stigmas are white.

Plant

A miniature bush of vigorous dwarf growth habit.

Foliage

Small size, normal in quantity. The new foliage is near Green 139A, and the old foliage is near Green 139A. Normal mid-stem leaves have five leaflets.

The leaflets are of an oval pointed shape, are smooth and glossy, and have a serrated edge. The serration is single and small in size. Petiole rachis is reddish and the petiole underside is rough with prickles. Stipules are long and serrated. The foliage is resistant to mildew under normal growing conditions at Irvine, Calif.

Wood

New wood is light green, with a smooth bark. Old wood is green with a smooth bark.

Prickles

There are many prickles on main canes from the base and on laterals from the main canes. The form is short and straight. Color when young is red.

Parentage

The seed parent was Petticoat, U.S. Plant Pat. No. 5,039. The pollen parent was Red Minimo, U.S. Plant Pat. No. 5,770.

Classification

Botanical is rosa hybrid. Commercial is miniature.

I claim:

1. A new and distinct variety of rose plant and parts thereof of the miniature class substantially as herein shown and described, characterized particularly as to novelty by the attractive high-centered white flowers, compact dwarf growth habit, rapid rooting and plant growth in pot culture, resistance to powdery mildew and presence of numerous flower clusters.

* * * * *

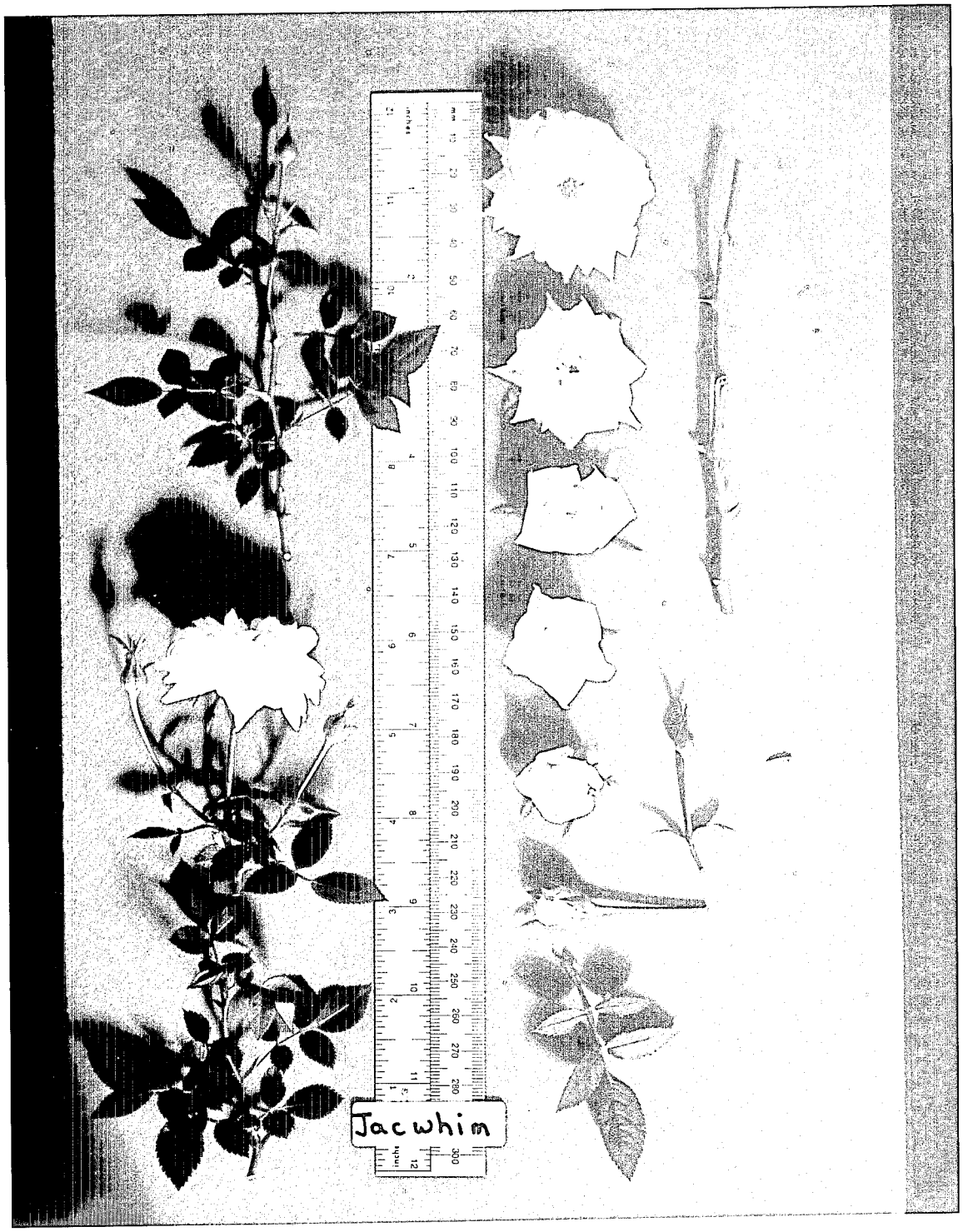
Jacwhim